United States Patent [19]

Nagase

[11] 4,148,625

[45] Apr. 10, 1979

[54] TETRAHYDROISOPHTHALIMIDE COMPOUNDS

[75] Inventor: Hiroshi Nagase, Kawanishi, Japan

[73] Assignee: Takeda Chemical Industries, Ltd., Osaka, Japan

[21] Appl. No.: 815,370

[22] Filed: Jul. 13, 1977

[30] Foreign Application Priority Data

Jul. 23, 1976 [JP] Japan ................................. 52-88414

[51] Int. Cl.[2] ...................... A01N 9/20; C07D 307/88
[52] U.S. Cl. ................................ 71/88; 260/343.3 R
[58] Field of Search ..................... 260/343.3 R; 71/88

[56] References Cited

U.S. PATENT DOCUMENTS

| 3,985,773 | 10/1976 | Alt et al. | 260/343.3 R |
| 3,990,880 | 11/1976 | Mumford | 260/343.3 R |

OTHER PUBLICATIONS

Howe J.O. Chem., vol. 38, 1973, pp. 4164–4167.
Roderick et al. J.O. Chem., vol 28, 1963, pp. 2018–2024.

*Primary Examiner*—Natalie Trousof
*Assistant Examiner*—Jane T. Fan
*Attorney, Agent, or Firm*—Burgess, Ryan and Wayne

[57] ABSTRACT

Tetrahydroisophthalimide compounds are useful for selective weed-controlling agents.

23 Claims, No Drawings

TETRAHYDROISOPHTHALIMIDE COMPOUNDS

This invention relates to novel tetrahydroisophthalimide compounds having weed-controlling activity, which compounds have the formula (I)

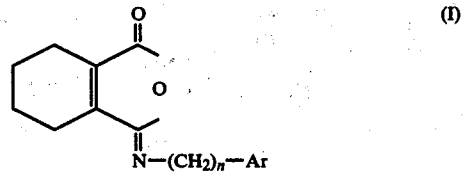

wherein n means 0 or 1 and Ar is a naphthyl group or a group represented by the formula

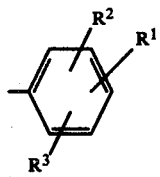

wherein $R^1$ is hydrogen, halogen, hydroxyl, nitro, trifluoromethyl, cyano, lower alkenyloxy, lower alkyl, lower alkoxy, lower alkylthio, aralkyloxy whose aryl group may optionally be mono- or di-substituted by the same or different members selected from the class consisting of halogens, nitro and lower alkyls, phenoxymethyloxy whose phenyl group may optionally be mono-substituted by halogen or aralkylthio whose aryl group may optionally be mono-substituted by halogen; $R^2$ is hydrogen, halogen, lower alkyl or lower alkoxy; $R^3$ is hydrogen or halogen, with the proviso that when $R^1$ is halogen and $R^3$ is hydrogen or halogen, $R^2$ is lower alkyl or lower alkoxy, when $R_2$ is halogen and $R^3$ is hydrogen or halogen, $R^1$ is hydroxyl, nitro, trifluoromethyl, cyano, lower alkenyloxy, lower alkyl, lower alkoxy, lower alkylthio, aralkyloxy whose aryl group may optionally be mono- or di-substituted by the same or different members selected from the class consisting of halogens, nitro and lower alkyls, phenoxymethyloxy whose phenyl group may optionally be mono-substituted by halogen or aralkylthio whose aryl group may optionally be mono-substituted by halogen and when each of $R^1$ and $R^2$ is hydrogen, $R^3$ is hydrogen.

More specifically, the present invention is directed to compounds of the formula

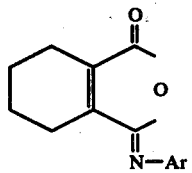

wherein Ar is:

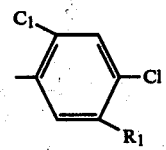

A1)

where $R_1$ is alkoxy or alkenyloxy having 1 to 5 carbon atoms:

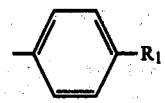

B1)

where $R_1$ is 4-methylbenzyloxy, 4-nitrobenzyloxy, 2,4-dichlorobenzyloxy, 3,4-dichlorobenzyloxy, 4-chlorobenzyloxy or benzyloxy; or

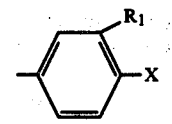

C1)

where X is chlorine or bromine and $R_1$ is alkoxy or alkenyloxy having 1 to 5 carbon atoms.

In another aspect, the invention relates to compositions containing the aforementioned compound for the control of undesirable vegetation.

Other nomenclature for the present tetrahydroisophthalimides is 3-arylimino-4,5,6,7-tetrahydro-1(3H)-isobenzofuranone.

The research undertaken by the present inventor into compounds that would have selective herbicidal activity led to the finding that compounds (I) are useful for the weed, control of undesired vegetation of monocots and dicots such as paddy-field weeds including barnyard grass [*Echinochloa Crus-Galli* Beauv.], umbrella plant [*Cyperus difformis* L. ], monochoria [*Monochoria vaginalis* presl], false pimpernel [*Lindernia procumbens* Philcox], toothcup [*Rotala indica* Koehne], spikerush [*Eleocharis acicularis* Roem. et Schult.], etc. and dry crop land weeds including Henr. crabgrass [*Digitaria adscendes* Henr.], pig weed [*Amaranthus retroflexus* L.]], lamb's quarters [*Chenopodium album* L.], inutade [*Polygonum Blumei* Meisn.] and common purslane [*Portulaca oleraca* L.], and that, particularly, compounds (I) of this invention display selective activity, when applied to the local soil, against afore-mentioned weeds without giving any substantial injury to particularly leguminous crop plants such as soybean as well as cotton. This invention is accomplished on the basis of the above new findings. Referring to the substituents $R^1$ to $R^3$ of the formula (II), the halogen atom is chlorine, bromine, iodine or fluorine. As the lower alkenyloxy group, there may be mentioned 1-propenyloxy or allyloxy (2-propenyloxy).

The lower alkyl group means a straight-chain or branched alkyl group of 1 to 6 carbon atoms, e.g. methyl, ethyl, propyl, isopropyl, butyl, sec. butyl, tert.butyl, isobutyl, pentyl, hexyl, etc. In particular, a lower alkyl group of 1 to 3 carbon atoms such as methyl, ethyl, propyl or isopropyl is perferable.

The lower alkoxy group is a group of 1 to 6 carbon atoms such as methoxy, ethoxy, propoxy, isopropoxy, butoxy, isobutoxy, sec.butoxy, pentyloxy or hexyloxy. Particularly preferred are lower alkoxy groups of 1 to 4 carbon atoms such as methoxy, ethoxy, propoxy, isopropoxy, butoxy, isobutoxy, etc.

The lower alkylthio group is a group of 1 to 3 carbon atoms such as methylthio, ethylthio or propylthio.

As examples of aralkyloxy group whose aryl group may optionally be mono- or di-substituted by the same or different members selected from the class consisting of halogens, nitro and lower alkyls, there may be mentioned benzyloxy, p-methylbenzyloxy, p-nitrobenzyloxy, p-chlorobenzyloxy, 2,4-dichlorobenzyloxy, 3,4-dichlorobenzyloxy, 2,6-dichlorobenzyloxy or 3,5-dichlorobenzyloxy etc.

As examples of phenoxymethyloxy group whose phenyl group may optionally be mono-substituted by halogen, there may be mentioned phenoxymethyloxy or p-chlorophenoxymethyloxy.

As examples of aralkylthio group whose aryl group may optionally be mono-substituted by halogen, there may be mentioned benzylthio or p-chlorobenzylthio.

The aforesaid substituents, the same or different, may be located in any appropriate position on the phenyl group.

Two sub-generic groups of compounds according to the invention are those where $R^1$ is lower alkenyloxy or lower alkoxy, $R^2$ is halogen, and $R^3$ is halogen or hydrogen; and where $R^1$ is aralkoxy whose aryl group may optionally be mono- or di-substituted by halogen or nitro and each of $R^2$ and $R^3$ is hydrogen.

The compound of the formula (I) can be produced, for example, by subjecting a compound of the formula (III) to dehydrative cyclization as schematically illustrated below.

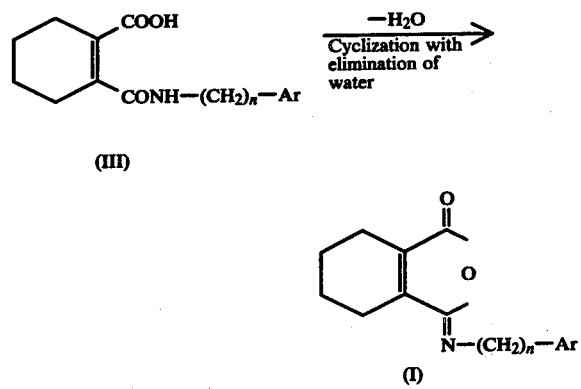

wherein Ar and n are respectively as defined hereinbefore.

Advantageously, the reaction is conducted under anhydrous conditions by permitting a dehydrating agent to act upon a compound (III) in an inert solvent. The dehydrating agent may, for example, be a carbodiimide derivative such as dicyclohexylcarbodiimide, diethylcarbodiimide or the like, a combination of a base with an acylating agent, or a combination of a base with an inorganic acid halide. As examples of said base, there may be mentiond pyridine, quinoline and other organic tertiary amines, e.g. dimethylaniline, triethylamine, trimethylamine, etc. as well as alkali metal carbonates and bicarbonates, such as sodium carbonate, sodium hydrogen carbonate, potassium carbonate, etc. The acylating agent may for example be a chloroformic acid ester (e.g. methyl chloroformate, ethyl chloroformate, etc.) or benzoyl chloride, and the inorganic acid halide may for example be phosgene, thionyl halide (e.g. thionyl chloride, thionyl bromide etc.) or phosphorus oxychloride. The proportion of said dehydrating agent based on each mole of compound (III) is normally in the range of about 1 to 2 mols and, preferably, in the range of about 1 to 1.2 mols. The reaction temperature is normally about 0° C to 50° C where a carbodiimide derivative is employed as the dehydrating agent, or normally in the range of about −15 to 60° C where a combination of a base with an acylating agent or with as inorganic acid halide is employed. The reaction time is normally about 30 minutes to about 3 hours. The inert solvents suitable for the purposes of this invention include hydrocarbons (e.g. benzene, toluene, hexane, cyclohexane, etc.), halogenated hydrocarbons (e.g. dichloromethane, carbon tetrachloride, chlorobenzene, etc.), diethyl ether, dioxane, tetrahydrofuran, acetonitrile, acetone, methyl ethyl ketone, ethyl acetate, nitrobenzene, etc.

The compound (I) obtained in the above manner can be isolated and purified by such known procedures as concentration, concentration under reduced pressure, distillation, solvent extraction, pH adjustment, phase transfer, crystallization, recrystallization, chromatographic separation, etc. The structural identity of compound (I) can be established based on its infrared absorption spectrum which shows the characteristic intense $v+0$ absorptions at 1760–1830 $cm^{-1}$ (Nujol mull). By the method of this invention, there can be produced the following compounds.

N-(3-isopropoxy-4-chlorophenyl)-3,4,5,6-tetrahydroisophthalimide

N-(2,4-dichloro-5-methoxyphenyl)-3,4,5,6-tetrahydroisophthalimide

N-(2,4-dichloro-5-ethoxyphenyl)-3,4,5,6tetrahydroisophthalimide

N-(2,4-dichloro-5-propoxyphenyl)-3,4,5,6-tetrahydroisophthalimide

N-(2,4-dichloro-5-isopropoxynyl)-3,4,5,6-tetrahydroisophthalimide

N-(2,4-dichloro-5-butoxyphenyl)-3,4,5,6-tetrahydroisophthalimide

N-(2,4-dichloro-5-isobutoxyphenyl)-3,4,5,6-tetrahydroisophthalimide

N-(2,4-dichloro-5-sec.butoxyphenyl)-3,4,5,6-tetrahydroisophthalimide

N-(2,4dichloro-5-pentyloxyphenyl)-3,4,5,6-tetrahydroisophthalimide

N-(2,4dichloro-5-isopentyloxyphenyl)-3,4,5,6-tetrahydroisophthalimide

N-(2,4-dichloro-5-allyloxyphenyl)-3,4,5,6-tetrahydroisophthalimide

N-[4-(4-methylbenzyloxy)-phenyl]3,4,5,6-tetrahydroisophthalimide

N-[4-(4-nitrobenzyloxy)-phenyl]-3,4,5,6-tetrahydroisophthalimide

N-[4-(2,4-dichlorobenzyloxy)-phenyl]-3,4,5,6-tetrahydroisophthalimide -tetrahydroisophthalimide N-[4-(4-chlorobenzyloxy)-phenyl]-3,4,5,6-tetrahydroisophthalimide N-(4-benzyloxyphenyl)-3,4,5,6-tetrahydroisophthalimide N-(3-isopropoxy-4-bromophenyl)-3,4,5,6-tetrahydroisophthalimide N-(3-allyloxy-4-bromophenyl)-3,4,5,6-tetrahydroisophthalimide N-(2,4-dichloro-5-methallyloxyphenyl)-3,4,5,6-tetrahydroisophthalimide Incidentally, N-phenyl-3,4,5,6-tetrahydrophthalamic acid, which falls within the range of starting material compounds (III) for this invention, has been described in Berichte der Deutschen Chemischem Gesellschaft 36,999 (1903) and other compounds of the formula (III) can also be produced, for example by the methods described in the literature cited hereinbefore or any method analogous thereto, as illustrated below.

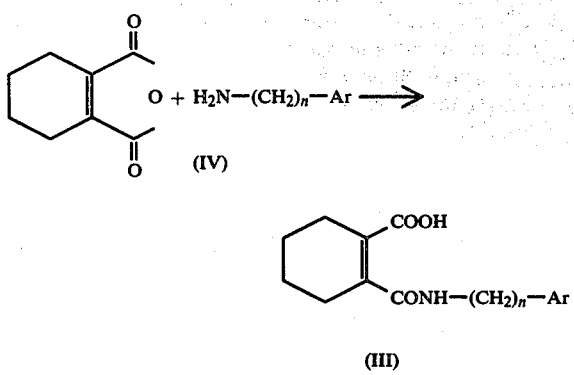

wherein Ar and n are respectively as defined hereinbefore. Thus, the compound (III) can be obtained, for example by reacting substantially equimolar amounts of 3,4,5,6-tetrahydrophthalic anhydride and an amine (IV) in an inert solvent, normally at a temperature of 10 to 90° C and preferably at a temperature of 20 to 60° C for a time from 5 minutes to one hour. As to the solvent employed for the purposes of this reaction, there may be mentioned benzene, toluene, hexane, dichloromethane, carbon tetrachloride, chlorobenzene, diethyl ether, dioxane, tetrahydrofuran, acetonitrille, acetone, methyl ethyl ketone and ethyl acetate, for example. The compound (III) can be isolated and purified by procedures conventional per se.

The compound of the formula (III) obtained as above need not necessarily be isolated and purified but may be subjected as such to dehydrative cyclization in accordance with this invention to obtain a compound of the formula (I) with advantage. The other starting material (IV) can be easily synthesized by one of the methods described, for example in Journal of the Chemical Society 91, 1543 (1907); Journal of the American Chemical Society 75, 2502 (1953), Journal of the Indian Chemical Society 43, 277 and Journal of the American Chemical Society 41, 450 (1919) or by a method analogous to any of those mentioned.

The compounds (I) according to this invention have herbicidal activity against the paddy-field weeds and dry-field weeds of the aforementioned varieties and find extensive use in controlling weeds in certain crops, such as rice, maize, soybean, cotton, etc. as applied to the local soil. The compounds (I) also have miticidal activity.

As a weed-controlling agent, the compounds (I) of this invention may be employed in the following manner. Thus, one or more of the compounds (I) are dissolved or dispersed in a suitable liquid carrier (e.g. solvent) or admixed with, or adsorbed on, a suitable solid carrier (e.g. diluent or adjuvant according to the intended application and, if necessary, an emulsifier, suspending agent, spreader-stickers, penetrant, wetting agent, viscosity builder, stabilizer, etc. are supplementally added. The compositions so formulated are used in such application forms as an oil suspension, emulsifiable concentrate, wettable powder, dust, granules, tablets, aerosols, ointments, etc. These application forms can be produced by procedures known per se.

While the concentration of the active compound in the weed-controlling composition should vary according to the intended application, suitable ranges are about 10 to 90 percent by weight in the case of emulsifiable concentrates, wettable powders, etc., about 0.1 to 10 weight percent in the case of such application forms as oils and dusts, and of the order of 1 to 20 weight percent for granules. These concentrations may be modified depending upon the purpose of application.

The emulsifiable concentrates or wettable powders, for instance, are preferably used as diluted (e.g. 100 to 100000-fold), for example with water, just prior to application.

As suitable examples of the liquid carrier employed in the weed-controlling composition of this invention, there may be mentioned water, alcohols (e.g. methyl alcohol, ethyl alcohol, ethylene glycol, etc.), ketones (e.g. acetone, methyl ethyl ketone, etc.), ethers (e.g. dioxane, tetrahydrofuran, cellosolve, etc.), aliphatic hydrocarbons (e.g. gasoline, kerosene, kerosin, fuel oil, machine oil, etc.), aromatic hydrocarbons (e.g. benzene, toluene, xylene, solvent naphtha, methyl naphthalene, etc.), halogenated hydrocarbons (e.g. chloroform, carbon tetrachloride, etc.), acid amides (e.g. dimethylformamide, etc.), esters (e.g. ethyl acetate, butyl acetate, glycerin fatty acid esters, etc.), nitriles (e.g. acetonitrile etc.) and so on. These solvents may be employed alone or as a mixture. As examples of said solid carrier (diluent, adjuvant), there may be mentioned vegetable powders (e.g. soybean flour, tobacco flour, wheat flour, sawdust, etc.), mineral powders such as clays (e.g. kaolin, bentonite, acid clay, etc.), talcs (e.g. talcum powder, alabaster) and silicious materials (e.g. diatomaceous earth, mica powder, etc.), alumina, sulfur powder, activated carbon, etc. These carriers are employed alone or as a mixture. The ointment basis may be selected from the group of such materials as polyethylene glycol, pectin, polyhydric alcohol esters of higher fatty acids (e.g. glycerin monostearate), cellulose derivatives (e.g. methylcellulose), sodium alginate, bentonite, higher alcohols, polyhydric alcohols (e.g. glycerin), petroleum jelly, white petroleum jelly, liquid paraffin, lard, various vegetable oils, lanolin, anhydrous lanolin, hydrogenated oils, waxes and resins. These materials may be employed alone or as a mixture, or as supplemented by surfactants or/and other materials.

As to the surfactants which may be relied on as emulsifiers, spreader-stickers, penetrants, dispersing agents, etc., there may be employed such products as soaps, polyoxyalkylaryl esters, alkylsulfates, alkylsulfonates, polyethylene glycol ethers, polyhydric alcohol esters and so on.

As a weed-controlling agent, the compound (I) is applied at a rate of about 5 to 50 grams, preferably about 10 to 40 grams, per are of a paddy-rice field, and at a rate of about 5 to 50 grams, preferably about 10 to 40 grams, per are of a crop land. The compound (I) is sparingly toxic to mammalian animals and fish, for instance, and can be used safely as agricultural aids.

Weed-controlling compositions containing the compound (I) may further contain any of such supplemental components as other herbicides, plant hormones, plant growth regulators, fungicides (e.g. copper type fungicides, organic chlorine fungicides, organosulfur fungicides, phenolic fungicides, etc.), insecticides (organophosphorus insecticides, natural insecticides, etc.), miticides, nematocides, synergists, attractants, repellents, pigments, fertilizers, etc. The following Reference Examples are given to illustrate the production of some representative compounds of the formula (III) and of the formula (IV).

REFERENCE EXAMPLE 1

(1) Production of 4-(2,4-dichlorobenzyloxy)-aniline

In ethanol, p-hydroxyacetoanilide is reacted with 2,4-dichlorobenzyl chloride in the presence of sodium ethoxide and the resultant 4-(2,4-dichlorobenzyloxy)-acetoanilide is treated with potassium hydroxide in ethanol, whereby 4-(2,4-dichlorobenzyloxy)-aniline is obtained as crystals melting at 70–71° C. In a similar manner, the following compounds can be prepared from the corresponding substituted benzyl halide derivatives.

| Compound | m.p. (°C.) |
|---|---|
| 4-(3,4-dichlorobenzyloxy)-aniline | 68 |
| 4-(p-methylbenzyloxy)-aniline | 105–106 |
| 4-(p-nitrobenzyloxy)-aniline | 122 |

(2) Production of 2,4-dihalogeno-5-substituted aniline

In glacial acetic acid, m-acetylaminophenol is brominated or chlorinated with 2 equivalents of bromine or chlorine gas as the case may be to obtain 2,4-dibromo- or 2,4-dichloro-5-acetylaminophenol. In ethanol, the last mentioned compound is reacted with an alkyl halide or the like corresponding to the 5-substituent group of the desired product. The following 2,4-dibromo- or 2,4-dichloro-5-substituted acetoanilide compounds are obtained in the same manner.

These acetoanilide derivatives can each be deacetylated with hydrochloric acid and neutralized with sodium hydroxide to obtain the corresponding aniline derivatives which, without prior isolation/purification, can be employed for reaction with 3,4,5,6-tetrahydrophthalic anhydride.

Reference Example 2

N-(4-chlorobenzyl)-3,4,5,6-tetrahydrophthalamic acid

4-Chlorobenzylamine hydrochloride (5.9 g) is suspended in benzene (30 ml) and neutralized by the dropwise addition of a 12% aqueous solution of sodium hydroxide (15 ml). The benzene layer is separated and filtered through a filter paper wetted with benzene. At room temperature, the filtrate is added dropwise to a solution of 3,4,5,6-tetrahydrophthalic anhydride (4.6 g) in benzene (50 ml) and the mixture is stirred at room temperature for 15 minutes. The precipitate is collected by filtration and washed with a small amount of benzene. Yield 8.7 g; m.p. 156–157° C.

The following compounds are obtained by procedures similar to those set forth in Reference Examples 1 and 2.

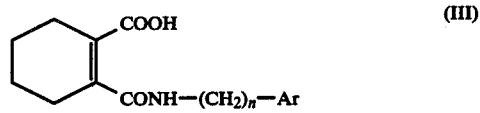

(III)

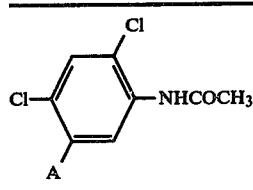

| A | m.p. (°C.) | B | m.p. (°C.) |
|---|---|---|---|
| i-C$_3$H$_7$O— | 127–129 | i-C$_3$H$_7$O— | 128 |
| n-C$_3$H$_7$O— | 124 | CH$_2$=CH—CH$_2$O— | 135 |
| n-C$_4$H$_9$O— | 99 | | |
| CH$_3$O— | 156 | | |
| C$_2$H$_5$O— | 141 | | |
| CH$_2$=CH—CH$_2$O— | 122–123 | | |
| 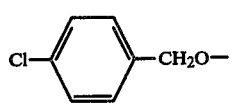 | 162 | | |

[wherein Ar and n are respectively as defined hereinbefore]

| —(CH$_2$)$_n$—Ar | m.p. (°C.) | —(CH$_2$)$_n$—Ar | m.p. (°C.) |
|---|---|---|---|
| 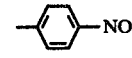 | 111–112 | 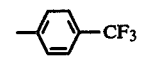 | 150–151 |
| 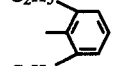 | 148–152 | 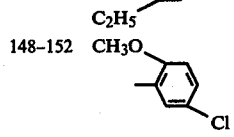 | 127–128 |
|  | 106–107 | | |

| —(CH$_2$)$_n$—Ar | m.p. (°C) | —(CH$_2$)$_n$—Ar | m.p. (°C) |
| --- | --- | --- | --- |
| 2,4-di-CH$_3$-C$_6$H$_3$— | 148–149 | 2,3-di-CH$_3$-C$_6$H$_3$— | 148–149 |
| 2,6-di-CH$_3$-C$_6$H$_3$— | 174–175 | 2,5-di-CH$_3$O-C$_6$H$_3$— | 103–104 |
| 4-n-C$_4$H$_9$-C$_6$H$_4$— | 140–142 | 2-CH$_3$-4-Cl-C$_6$H$_3$— | 146–147 |
| 3-CH$_3$-4-NO$_2$-C$_6$H$_3$— | 100–105 | 4-CN-C$_6$H$_4$— | 103–104 |
| 4-SCH$_3$-C$_6$H$_4$— | 133 | 4-(4-CH$_3$-C$_6$H$_4$-OCH$_2$)-C$_6$H$_4$— | 144–145 |
| 4-(4-Cl-C$_6$H$_4$-O-CH$_2$)-C$_6$H$_4$— | 139–140 | 2-O-i-C$_3$H$_7$-4,5-di-Cl-C$_6$H$_2$— | 98–100 |
| 4-(2,4-di-Cl-C$_6$H$_3$-OCH$_2$)-C$_6$H$_4$— | 153–154 | 2-O-i-C$_3$H$_7$-4-Cl-C$_6$H$_3$— | 122–124 |
| 4-(2,6-di-Cl-C$_6$H$_3$-OCH$_2$)-C$_6$H$_4$— | 168–169 |  |  |
| 2,4-di-Br-5-(O-CH$_2$CH=CH$_2$)-C$_6$H$_2$— | 118–120 | 2,4-di-Cl-5-(O-CH$_2$O-C$_6$H$_4$-4-Cl)-C$_6$H$_2$— | 106–109 |
| 2,4-di-Cl-5-OC$_2$H$_5$-C$_6$H$_2$— | 119–124 |  |  |

Notes:
1. n: normal
2. i: iso

EXAMPLE 1

N-[4-(4-chlorobenzyloxy)-phenyl]-3,4,5,6-tetrahydroisophthalimide (Compound No. 1)

1) In dry benzene (30 ml) is suspended N-[4-(4-chlorobenzyloxy)-phenyl]-3,4,5,6-tetrahydrophthalamic acid (3.9 g), followed by the addition of dicyclohexylcarbodiimide (2.5 g). The mixture is stirred at room temperature for 2 hours, after which time the insolubles are filtered off. The filtrate is concentrated at reduced temperature and pressure. To the oily residue is added a small amount of n-hexane and the mixture is allowed to stand. The resultant crystals are collected by filtration and washed with n-hexane. Yield 2.6 g; m.p. 125–129° C. The above crystals are recrystallized from benzene-n-hexane. The above procedure yields crystals melting at 129–130° C. Infrared absorption spectrum ($\mu$C=O) 1795 cm$^{-1}$.

2) In benzene (130 ml) is suspended N-[4-(4-chlorobenzyloxy)-phenyl]-3,4,5,6-tetrahydrophthalamic acid (18.1 g), followed by the addition of pyridine (6.8 g). While the mixture is stirred at a constant temperature of 4–9° C, a solution of thionyl chloride (5.4 g) in benzene (10 ml) is added dropwise over a period of 6 minutes. The mixture is further stirred at that temperature for 40 minutes, after which time the insolubles are filtered off. The filtrate is concentrated to dryness at reduced temperature and pressure. The resultant crystals are dissolved in benzene and the insolubles, occurring in minor amounts, are filtered off. The resultant filtrate is concentrated to dryness at reduced temperature and pressure. Yield 11.4 g; m.p. 129–130 C.

EXAMPLE 2

N-(4-nitrophenyl)-3,4,5,6-tetrahydroisophthalimide (Compound No. 2)

In benzene (100 ml) is suspended N-(4-nitrophenyl)-3,4,5,6-tetrahydrophthalamic acid (10 g), followed by the addition of pyridine (5.6 g). While the mixture is stirred at 5–10° C, a solution of thionyl chloride (4.3 g) in benzene (10 ml) is added dropwise over a period of 8 minutes. The reaction mixture is further stirred at that temperature for one hour. The insolubles are filtered off and the filtrate is concentrated to dryness at reduced pressure and temperature. The crystals are washed with n-hexane. Yield 8.2 g; m.p. 80–85° C. Upon recrystallization from benzene-n-hexane, crystals melting at 85–86° C are obtained. Infrared absorption spectrum ($v$C=O) 1810 cm$^{-1}$, 1780 cm$^{-1}$.

EXAMPLE 3

By procedures similar to those set forth above in Examples 1 and 2, the following compounds No. 3 to 74 are obtained from the corresponding compounds (III). (These compounds are shown in Table 1

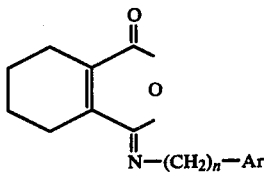 (I)

[wherein Ar and n are respectively as previously defined]

Table 1

| No | —(CH₂)ₙ—Ar | m.p. (°C.) |
|---|---|---|
| 3 | C₆H₅—CH₂— | 93–94 |
| 4 | 2-Cl-C₆H₄—CH₂— | 114–115 |
| 5 | 4-Cl-C₆H₄—CH₂— | 117–118 |
| 6 | 2-CH₃-C₆H₄— | 97 |
| 7 | 3-CH₃-C₆H₄— | 68–69 |
| 8 | 4-CH₃-C₆H₄— | 103–104 |
| 9 | 4-n-C₄H₉-C₆H₄— | Oil B 0.05 170° C. |
| 10 | 4-C₂H₅-C₆H₄— | 59–60 |
| 11 | 4-(CH₃)₃C-C₆H₄— | 92.5–93.5 |
| 12 | 2-OCH₃-C₆H₄— | 122–124 |
| 13 | 3-CH₃O-C₆H₄— | 62 |
| 14 | 4-CH₃O-C₆H₄— | 99 |
| 15 | 3-C₂H₅O-C₆H₄— | 77–78 |
| 16 | 4-C₂H₅O-C₆H₄— | 88–89 |
| 17 | 4-(CH₃)₂CH-O-C₆H₄— | 88–89 |
| 18 | 4-n-C₄H₉O-C₆H₄— | 74 |
| 19 | 4-n-C₅H₁₁O-C₆H₄— | 59–61 |
| 20 | 4-n-C₆H₁₃O-C₆H₄— | 57–59 |
| 21 | 3-CH₂=CH—CH₂O-C₆H₄— | 61 |
| 22 | 4-CH₂=CH—CH₂O-C₆H₄— | 96–97 |
| 23 | 4-C₆H₅CH₂O-C₆H₄— | 121–123 |
| 24 | 4-(4-CH₃-C₆H₄-CH₂O)-C₆H₄— | 152–154 |
| 25 | 4-(4-O₂N-C₆H₄-CH₂O)-C₆H₄— | 155–156.5 |
| 26 | 4-(3,4-Cl₂-C₆H₃-CH₂O)-C₆H₄— | 132–133 |
| 27 | 4-(2,4-Cl₂-C₆H₃-CH₂O)-C₆H₄— | 118–119 |
| 28 | 3-HO-C₆H₄— | 138 |
| 29 | 4-HO-C₆H₄— | 147–148 |
| 30 | 4-O₂N-C₆H₄— | 105–106 |
| 31 | 2-CF₃-C₆H₄— | 98 |
| 32 | 4-CF₃-C₆H₄— | 64–65 |
| 33 | 4-NC-C₆H₄— | 95–97 |
| 34 | 4-CH₃S-C₆H₄— | 80–81 |
| 35 | 4-(4-Cl-C₆H₄-CH₂S)-C₆H₄— | 105–106 |
| 36 | 1-naphthyl | 134.5–135.5 |
| 37 | 2-OCH₃-4-CH₃-C₆H₃— | 88–90 |
| 38 | 4-Cl-2-CH₃-C₆H₃— | 96–97 |
| 39 | 2-Cl-4-CH₃-C₆H₃— | 88–89 |
| 40 | 2-Cl-3-CH₃-C₆H₃— | 113–115 |
| 41 | 4-Br-2-CH₃-C₆H₃— | 97–99 |
| 42 | 4-Cl-2-OCH₃-C₆H₃— | 97–98 |
| 43 | 2,4-(CH₃)₂-C₆H₃— | 121–122 |
| 44 | 3,5-(CH₃)₂-C₆H₃— | 94–95 |

Table 1-continued

| No | —(CH$_2$)$_n$—Ar | m.p. (°C) |
|---|---|---|
| 45 | 2,6-(CH$_3$)$_2$-C$_6$H$_3$- | 104–105 |
| 46 | 2,4-(CH$_3$)$_2$-C$_6$H$_3$- | 81–82 |
| 47 | 2,5-(CH$_3$)$_2$-C$_6$H$_3$- | 67–68 |
| 48 | 3,4-(CH$_3$)$_2$-C$_6$H$_3$- | 126–127 |
| 49 | 2,6-(C$_2$H$_5$)$_2$-C$_6$H$_3$- | 47–48 |
| 50 | 2-CH$_3$-4-O$_2$N-C$_6$H$_3$- | 96–97 |
| 51 | 3-CH$_3$-4-O$_2$N-C$_6$H$_3$- | 108 |
| 52 | 3,4-(CH$_3$O)$_2$-C$_6$H$_3$- | 118–119 |
| 53 | C$_6$H$_5$- | 73–75 |
| 54 | 2-CF$_3$-4-Cl-C$_6$H$_3$- | 93–95.5 |
| 55 | 2,4-Cl$_2$-5-CH$_3$O-C$_6$H$_2$- | 149–150 |
| 56 | 2,4-Cl$_2$-5-C$_2$H$_5$O-C$_6$H$_2$- | 87–89 |
| 57 | 2,4-Cl$_2$-5-n-C$_3$H$_7$O-C$_6$H$_2$- | 77 |
| 58 | 2,4-Cl$_2$-5-i-C$_3$H$_7$O-C$_6$H$_2$- | 103–104 |
| 59 | 2,4-Cl$_2$-5-n-C$_4$H$_9$O-C$_6$H$_2$- | 55–56 |
| 60 | 2,4-Cl$_2$-5-i-C$_4$H$_9$O-C$_6$H$_2$- | 82–83 |
| 61 | 2,4-Cl$_2$-5-sec-C$_4$H$_9$O-C$_6$H$_2$- | 64 |
| 62 | 2,4-Cl$_2$-5-n-C$_5$H$_{11}$O-C$_6$H$_2$- | 61–62 |
| 63 | 2,4-Cl$_2$-5-i-C$_5$H$_{11}$O-C$_6$H$_2$- | 68.5–69.5 |
| 64 | 2,4-Cl$_2$-5-(CH$_2$=CH—CH$_2$O)-C$_6$H$_2$- | 101–102 |
| 65 | 2,4-Cl$_2$-5-(4-Cl-C$_6$H$_4$-CH$_2$O)-C$_6$H$_2$- | 143–144 |
| 66 | 2,4-Br$_2$-5-i-C$_3$H$_7$O-C$_6$H$_2$- | 122–123 |
| 67 | 2,4-Br$_2$-5-(CH$_2$=CH—CH$_2$O)-C$_6$H$_2$- | 106–108 |
| 68 | 3-i-C$_5$H$_{11}$O-C$_6$H$_4$- | oil $N_D^{23}$ 1.5775 |
| 69 | 2-Cl-5-i-C$_3$H$_7$O-C$_6$H$_3$- | 97–98 |
| 70 | 2-Cl-5-(4-CH$_3$-C$_6$H$_4$-OCH$_2$)-C$_6$H$_3$- (4-Cl-C$_6$H$_4$-OCH$_2$-C$_6$H$_4$-) | 99–101 |
| 71 | 2,4-Cl$_2$-5-(CH$_2$=C(CH$_3$)—CH$_2$O)-C$_6$H$_2$- | 122–123 |
| 72 | 2,4-Cl$_2$-5-(4-Cl-C$_6$H$_4$-OCH$_2$)-C$_6$H$_2$- | 124–126 |
| 73 | 2-Br-5-i-C$_3$H$_7$O-C$_6$H$_3$- | 95–97 |
| 74 | 2-Br-5-(CH$_2$=CH—CH$_2$—O)-C$_6$H$_3$- | 101–102 |

Notes
1. n: normal
2. i: iso
3. sec: secondary
4. B 0.05°C.: b.p. under a pressure of 0.05 mmHg
5. $N_D^{23}$: Refractive index against sodium D-line at 23° C.

EXAMPLE 4

An emulsifiable composition containing 20 weight % of N-[4-(4-chlorobenzyloxy)phenyl]-3,4,5,6-tetrahydroisophthalimide, 57 weight % of xylene and 5 weight % of polyethylene glycol ether.

EXAMPLE 5

1/5000-are Wagner pots were packed with paddyfield soil and respectively sown with seeds of *Echinochloa Crus-galli* Beauv., *Cyperus difformis* L., *Monochoria vaginalis* presl, *Lindernia Procumbens* Philcox and *Rotala indica* Koehne. Then, the paddyfield soil including the over-the winter shoots of *Eleocharis acicularis*

Roem.et Schult. was sprinkled over the seeds. At the same time, rice seedlings (variety: Manryo; 2.0 leaves, 12 cm tall, grown in a separate nursery) were transplanted and each pot was filled with water to a depth of 3 cm above the soil surface. Then, granules of the formulation containing 10 weight % of the compound of the formula (I), 5 weight % of sodium lignosulfonate and 85 weight % of bentonite as compounded together with water were applied to the cover water in each pot at the rates of 10 g, 20 g and 40 g as the active ingredient (compound (I)) per are. 21 days after the application of the test compositions, the weed-controlling activity and phytotoxicity of each compound were investigated. The weed-controlling effects were scored and rated according to the following scheme of indices.

Index 0 — No effect [0% inhibition (herbicidal)]
Index 1 — Slightly effective [0.1-50% " ]
Index 2 — Somewhat effective [50.1-70% " ]
Index 3 — Moderately effective [70.1-87.5% inhibition herbicidal)]
Index 4 — Highly effective [87.6-99.9% " ]
Index 5 — Exceedingly effective [100% " ]

The phytotoxcity (degree of injury) of each composition to price plants was scored on the following scale.
Index 0 — No injury (0% injury)
Index 1 — Little injurious (0.1-12.5% " ) Index 2 — Slightly injurious (12.6-30.0% " )
Index 3 — Somewhat injurious (30.1-50.0% " )
Index 4 — Very injurious (50.1-99.9% " )
Index 5 Exceedingly injurious (100% " )

The scores are set forth in Table 2.

Table 2

| Compound No. | Dose g/are | Rice | Echinochloa crusgalli Beauv. | Cyperus difformis L. | Monochoria vaginalis Presl | Lindernia Procumbens Philcox | Rotala indicia Koehne | Eleocharis acicularis Roem.et Schult. |
|---|---|---|---|---|---|---|---|---|
| 1 | 10 | 0 | 5 | 5 | 5 | 5 | 5 | 5 |
|   | 20 | 1 | 5 | 5 | 5 | 5 | 5 | 5 |
| 5 | 20 | 0 | 2 | 5 | 5 | 5 | 5 | 4 |
|   | 40 | 1 | 5 | 5 | 5 | 5 | 5 | 4 |
| 14 | 20 | 0 | 1 | 5 | 5 | 4 | 4 | 5 |
|   | 40 | 0 | 1 | 5 | 5 | 5 | 5 | 5 |
| 26 | 10 | 1 | 1 | 5 | 5 | 5 | 5 | 3 |
|   | 20 | 1 | 2 | 5 | 5 | 5 | 5 | 3 |
| 27 | 10 | 1 | 4 | 5 | 5 | 5 | 5 | 3 |
|   | 20 | 1 | 4 | 5 | 5 | 5 | 5 | 5 |
| 24 | 20 | 1 | 4 | 5 | 5 | 5 | 5 | 4 |
|   | 40 | 1 | 5 | 5 | 5 | 5 | 5 | 5 |
| 32 | 40 | 0 | 2 | 5 | 5 | 5 | 5 | 5 |
| 33 | 10 | 2 | 0 | 5 | 5 | 4 | 4 | 4 |
|   | 20 | 3 | 1 | 5 | 5 | 5 | 5 | 5 |
|   | 20 | 0 | 3 | 5 | 5 | 5 | 5 | 4 |
| 35 | 40 | 1 | 5 | 5 | 5 | 5 | 5 | 4 |
| 36 | 10 | 1 | 3 | 5 | 4 | 5 | 5 | 5 |
|   | 20 | 2 | 3 | 5 | 5 | 5 | 5 | 5 |
| 38 | 10 | 0 | 0 | 5 | 4 | 4 | 4 | 4 |
|   | 20 | 1 | 2 | 5 | 5 | 5 | 5 | 5 |
| 40 | 20 | 1 | 2 | 5 | 5 | 4 | 4 | 3 |
| 43 | 40 | 0 | 0 | 5 | 3 | 3 | 3 | 4 |
| 44 | 20 | 0 | 0 | 5 | 4 | 5 | 5 | 4 |
|   | 40 | 1 | 1 | 5 | 5 | 5 | 5 | 5 |
| 55 | 10 | 1 | 1 | 5 | 5 | 5 | 5 | 5 |
|   | 20 | 2 | 5 | 5 | 5 | 5 | 5 | 5 |
| 56 | 10 | 2 | 4 | 5 | 5 | 5 | 5 | 5 |
|   | 20 | 3 | 5 | 5 | 5 | 5 | 5 | 5 |
| 57 | 10 | 1 | 5 | 5 | 5 | 5 | 5 | 4 |
|   | 20 | 1 | 5 | 5 | 5 | 5 | 5 | 5 |
| 58 | 10 | 1 | 5 | 5 | 5 | 5 | 5 | 4 |
|   | 20 | 1 | 5 | 5 | 5 | 5 | 5 | 5 |
| 59 | 10 | 1 | 5 | 5 | 5 | 5 | 5 | 4 |
|   | 20 | 2 | 5 | 5 | 5 | 5 | 5 | 5 |
| 39 | 40 | 0 | 2 | 5 | 5 | 5 | 5 | 5 |
| 73 | 2.5 | 1 | 4 | 5 | 5 | 5 | 5 | 5 |
| 74 | 2.5 | 1 | 4 | 5 | 5 | 5 | 5 | 5 |
| Control | — | 0 | 0 | 0 | 0 | 0 | 0 | 0 |

Table 2-continued

| Compound No. | Dose g/are | Rice | Echinochloa crusgalli Beauv. | Cyperus difformis L. | Monochoria vaginalis Presl | Lindernia Procumbens Philcox | Rotala indicia Koehne | Eleocharis acicularis Roem.et Schult. |
| --- | --- | --- | --- | --- | --- | --- | --- | --- |
| (untreated) | | | | | | | | | and injuries to rice plants were investigated and rated on the same scale as that used in Example 5.

Table 3

| Compound No. | Dose g/are | Rice | Echinochloa crusgalli Beauv. | Cyperus difformis L. | Monochoria vaginalis Presl | Lindernia Procumbens Philcox | Rotala indicia Koehne | Eleocharis acicularis Roem.et Schult. |
| --- | --- | --- | --- | --- | --- | --- | --- | --- |
| 1 | 10 | 1 | 5 | 5 | 5 | 5 | 5 | 4 |
|  | 20 | 1 | 5 | 5 | 5 | 5 | 5 | 5 |
| 14 | 20 | 0 | 4 | 4 | 4 | 3 | 3 | 2 |
|  | 40 | 1 | 5 | 5 | 4 | 4 | 4 | 4 |
| 27 | 10 | 0 | 1 | 3 | 4 | 4 | 4 | 1 |
|  | 20 | 1 | 2 | 5 | 5 | 5 | 5 | 3 |
| 38 | 20 | 0 | 3 | 5 | 3 | 4 | 4 | 3 |
|  | 40 | 0 | 4 | 5 | 4 | 4 | 4 | 4 |
| 56 | 10 | 2 | 5 | 5 | 4 | 5 | 5 | 3 |
|  | 20 | 3 | 5 | 5 | 5 | 5 | 5 | 4 |
| 57 | 10 | 1 | 4 | 5 | 5 | 5 | 5 | 3 |
|  | 20 | 2 | 5 | 5 | 5 | 5 | 5 | 4 |
| 58 | 10 | 1 | 4 | 5 | 2 | 4 | 4 | 2 |
|  | 20 | 1 | 5 | 5 | 4 | 4 | 4 | 3 |
| 59 | 10 | 1 | 2 | 4 | 4 | 4 | 4 | 2 |
|  | 20 | 1 | 3 | 5 | 4 | 5 | 5 | 3 |
| 55 | 10 | 1 | 2 | 5 | 4 | 4 | 4 | 2 |
|  | 20 | 2 | 4 | 5 | 4 | 5 | 5 | 4 |
| 73 | 10 | 1 | 5 | 5 | 4 | 5 | 5 | 5 |
| 74 | 10 | 2 | 5 | 5 | 4 | 5 | 5 | 5 |
| Control (untreated) | — | 0 | 0 | 0 | 0 | 0 | 0 | 0 |

EXAMPLE 6

1/5000-are Wagner pots were packed with paddy-field soil and respectively sown with seeds of *Cyperus difformis* L., *Monochoria vaginalis* Presl, *Lindernia Procumbens* Philcox. and *Rotala indica* Koehne. Then, paddyfield soil including the over-the-winter shoots of *Eleocharis acicularis* Roem. et Schult. was sprinkled over the seeds. Five days later, seeds of *Echinochloa crus-galli* Beauv. were sown. Then, rice seedings similar to those used in Example 5 were transplanted and the pots were filled with water to a depth of 3 cm above the soil surface. After a week when *Echinochloa* plants had reacted the one-leaf stage or thereabouts, granules of the same formulation as that of Example 5 were applied to the cover water at the rates of 10 g, 20 g and 40 g as the active compound. Twenty-one days following the application of the compositions, the herbicidal effects

EXAMPLE 7

900 cm$^2$-Plastic pots were packed with crop-field soil and sown with seeds of *Digitaria adscendes* Henr., *Amaranthus retroflexus* L., *Chenopodium album* L., *Polygonum Blumei* Meisn. and *Portulaca oleracea* L.

Then, corn (maize), soybean and cotton seeds were sown in rows, followed by the application of cover soil in a thickness of 0.5 cm. An emulsifiable concentrate containing 20 weight % of compound (I), similar to that prepared in Example 4, was diluted with water and evenly applied to the soil by means of a spray-gun at rates of 20 g and 40 g as the active compound (I) per are. After 30 days, the action on weeds and harm to crop plants of each composition were investigated and scored on the same scale as that used in Example 5. The results are set forth in Table 4.

Table 4

| Compound No. | Dose g/are | Digitaria adscendes Henr. | Amaranthus retroflexus L. | Chenopodium album L. | Polygonum Blumei Meisn. | Portulaca oleracea L. | Corn | Soybean | Cotton |
|---|---|---|---|---|---|---|---|---|---|
| 1 | 20 | 4 | 5 | 5 | 3 | 5 | 1 | 0 | 0 |
| 2 | 20 | 1 | 5 | 4 | 3 | 5 | 0 | 0 | 0 |
| 8 | 20 | 5 | 5 | 5 | 5 | 5 | 1 | 0 | 0 |
| 10 | 20 | 4 | 5 | 3 | 4 | 5 | 0 | 0 | 0 |
| 14 | 20 | 4 | 4 | 4 | 4 | 5 | 0 | 1 | 0 |
| 16 | 20 | 2 | 3 | 3 | 2 | 5 | 0 | 0 | 0 |
| 21 | 40 | 2 | 4 | 4 | 4 | 5 | 0 | 0 | 0 |
| 22 | 40 | 3 | 5 | 4 | 3 | 5 | 0 | 0 | 0 |
| 23 | 20 | 2 | 5 | 4 | 4 | 5 | 0 | 0 | 0 |
| 24 | 20 | 4 | 5 | 4 | 3 | 5 | 0 | 0 | 0 |
| 25 | 40 | 1 | 5 | 4 | 1 | 4 | 0 | 0 | 1 |
| 32 | 20 | 4 | 5 | 5 | 5 | 5 | 1 | 1 | 0 |
| 33 | 20 | 4 | 5 | 5 | 4 | 5 | 0 | 0 | 0 |
| 35 | 20 | 1 | 4 | 2 | 1 | 4 | 0 | 0 | 0 |
| 36 | 20 | 4 | 5 | 5 | 4 | 5 | 1 | 0 | 0 |
| 38 | 20 | 5 | 5 | 5 | 4 | 5 | 1 | 0 | 0 |
| 40 | 20 | 1 | 1 | 2 | 1 | 4 | 0 | 0 | 0 |
| 41 | 40 | 5 | 5 | 5 | 4 | 5 | 0 | 0 | 0 |
| 44 | 20 | 2 | 3 | 1 | 1 | 5 | 0 | 0 | 0 |
| 50 | 20 | 2 | 4 | 4 | 1 | 5 | 0 | 0 | 0 |
| 53 | 20 | 4 | 4 | 4 | 3 | 3 | 0 | 0 | 0 |
| 55 | 20 | 4 | 5 | 5 | 4 | 5 | 0 | 0 | 0 |
| 56 | 40 | 5 | 5 | 5 | 5 | 5 | 1 | 0 | 0 |
| 57 | 40 | 4 | 5 | 5 | 4 | 5 | 0 | 0 | 0 |
| 58 | 20 | 5 | 5 | 5 | 5 | 5 | 0 | 0 | 0 |
| 59 | 40 | 4 | 5 | 4 | 2 | 5 | 0 | 0 | 0 |
| 60 | 40 | 3 | 5 | 5 | 2 | 5 | 0 | 0 | 0 |
| 62 | 40 | 4 | 5 | 4 | 4 | 5 | 1 | 0 | 0 |
| 64 | 40 | 5 | 5 | 5 | 5 | 5 | 0 | 0 | 0 |
| 71 | 40 | 3 | 4 | 4 | 5 | 4 | 1 | 0 | 0 |
| 73 | 10 | 4 | 5 | 5 | 5 | 5 | 1 | 0 | 1 |
| 74 | 20 | 4 | 4 | 5 | 4 | 5 | 1 | 0 | 1 |
| Control (untreated) | — | 0 | 0 | 0 | 0 | 0 | 0 | 0 | 0 |

What is claimed is:

1. A compound of the formula

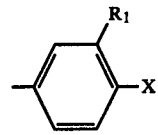

wherein Ar is:

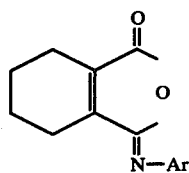

where $R_1$ is alkoxy or alkenyloxy having 1 to 5 carbon atoms;

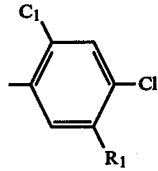

where $R_1$ is 4-methylbenzyloxy, 4-nitrobenzyloxy, 2,4-dichlorobenzyloxy, 3,4-dichlorobenzyloxy, 4-chlorobenzyloxy or benzyloxy; or

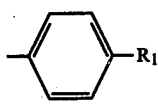

where X is chlorine or bromine and $R_1$ is alkoxy or alkenyloxy having 1 to 5 carbon atoms.

2. A compound as claimed in claim 1, wherein the compound is N-(3-isopropoxy-4-chlorophenyl)-3,4,5,6-tetrahydroisophthalimide.

3. A compound as claimed in claim 1, wherein the compound is N-(2,4-dichloro-5-methyloxyphenyl)-3,4,5,6-tetrahydroisophthalimide.

4. A compound as claimed in claim 1, wherein the compound is N-(2,4-dichloro-5-ethoxyphenyl)-3,4,5,6-tetrahydroisophthalimide.

5. A compound as claimed in claim 1, wherein the compound is N-(2,4-dichloro-5-propoxyphenyl)-3,4,5,6-tetrahydroisophthalimide.

6. A compound as claimed in claim 1, wherein the compound is N-(2,4-dichloro-5-isopropoxyphenyl)-3,4,5,6-tetrahydroisophthalimide.

7. A compound as claimed in claim 1, wherein the compound is N-(2,4-dichloro-5-butoxyphenyl)-3,4,5,6-tetrahydroisophthalimide.

8. A compound as claimed in claim 1, wherein the compound is N-(2,4-dichloro-5-isobutoxyphenyl)-3,4,5,6-tetrahydroisophthalimide.

9. A compound as claimed in claim 1, wherein the compound is N-(2,4-dichloro-5-sec.butoxyphenyl)-3,4,5,6-tetrahydroisophthalimide.

10. A compound as claimed in claim 1, wherein the compound is N-(2,4-dichloro-5-pentyloxyphenyl)-3,4,5,6-tetrahydroisophthalimide.

11. A compound as claimed in claim 1, wherein the compound is N-(2,4-dichloro-5-isopentyloxyphenyl)-3,4,5,6-tetrahydroisophthalimide.

12. A compound as claimed in claim 1, wherein the compound is N-(2,4-dichloro-5-allyloxyphenyl)-3,4,5,6-tetrahydroisophthalimide.

13. A compound as claimed in claim 1, wherein the compound is N-[4-(4-methylbenzyloxy)-phenyl]-3,4,5,6-tetrahydroisophthalimide.

14. A compound as claimed in claim 1, wherein the compound is N-[4-(4-nitrobenzyloxy)-phenyl]-3,4,5,6-tetrahydroisophthalimide.

15. A compound as claimed in claim 1, wherein the compound is N-[4-(2,4-dichlorobenzyloxy)-phenyl]-3,4,5,6-tetrahydroisophthalimide.

16. A compound as claimed in claim 1, wherein the compound is N-[4-(3,4-dichlorobenzyloxy)-phenyl]-3,4,5,6-tetrahydroisophthalimide.

17. A compound as claimed in claim 1, wherein the compound is N-[4-(4-chlorobenzyloxy)-phenyl]-3,4,5,6-tetrahydroisophthalimide.

18. A compound as claimed in claim 1, wherein the compound is N-(4-benzyloxyphenyl)-3,4,5,6-tetrahydroisophthalimide.

19. A compound as claimed in claim 1, wherein the compound is N-(3-isopropoxy-4-bromophenyl)-3,4,5,6-tetrahydroisophthalimide.

20. A compound as claimed in claim 1, wherein the compound is N-(3-allyloxy-4-bromophenyl)-3,4,5,6-tetrahydroisophthalimide.

21. A compound as claimed in claim 1, wherein the compound is N-(2,4-dichloro-5-methallyloxyphenyl)-3,4,5,6-tetrahydroisophthalimide.

22. A composition for the control of undesirable vegetation which comprises an effective amount of the compound of claim 1 and at least one of an emulsifier and a solid or liquid carrier.

23. A method of controlling weeds comprising applying an effective amount of the composition of claim 22 to the area to be controlled.--

* * * * *

UNITED STATES PATENT OFFICE
CERTIFICATE OF CORRECTION

Patent No. 4,148,625       Dated April 10, 1979

Inventor(s) Hiroshi Nagase

It is certified that error appears in the above-identified patent and that said Letters Patent are hereby corrected as shown below:

Column 2, line 47:  "Referring" should begin a new paragraph.

Column 4, line 18:  "v+0" should be --vc=0--;  "cm$^{31}$ $^1$(Nujol" should be --cm$^{-1}$ (Nujol--.

line 19:  "By" should start a new paragraph.

line 21:  "4chlorophenyl" should be --4-chlorophenyl--.

line 25:  "3,4,5,6tetrahy-" should be --3,4,5,6-tetrahy- --.

line 30:  "isopropoxynyl" should be --isopropoxyphenyl--.

line 38:  "2,4dichloro" should be --2,4-dichloro--.

line 40:  "2,4dichloro" should be --2,4-dichloro--.

line 49:  Cancel "-tetrahydroisophthalimide".

between lines 49 and 50:  Insert the following: --N-[4-(3,4-dichlorobenzyloxy)-phenyl]-3,4,5,6-tetrahydroisophthalimide--.

line 54:  "N-(3-isopropoxy-4-bromophenyl...." should begin a new paragraph.

UNITED STATES PATENT OFFICE
CERTIFICATE OF CORRECTION

Patent No. 4,148,625              Dated April 10, 1979

Inventor(s) Hiroshi Nagase

It is certified that error appears in the above-identified patent and that said Letters Patent are hereby corrected as shown below:

Column 5, line 26: "acetonitrille" should be --acetonitrile--.

Column 9, line 59: "µ" should be -- ν --.

Columns 11 & 12   should be inserted.  See Attachment (This correction applys to the Grant, exclusively)

Column 14, line 68: "over-the winter" should be --over-the-winter--.

Column 16, line 11: "Index 2—" should begin a new paragraph.

line 15: "Index 5 Exceedingly" should be --Index 5 —— Exceedingly--.

Table 2: The groupings are incorrect. The compounds are not grouped with correct "Dose g/are". The following are the corrected entries:

| | |
|---|---|
| Compound No. 1: | 10 |
| | 20 |
| Compound No. 5: | 20 |
| | 40 |
| Compound No. 14: | 20 |
| | 40 |

UNITED STATES PATENT OFFICE
CERTIFICATE OF CORRECTION

Patent No. 4,148,625　　　　Dated April 10, 1979

Inventor(s) Hiroshi Nagase

It is certified that error appears in the above-identified patent and that said Letters Patent are hereby corrected as shown below:

Column 16, Table 2 corrected entries continued:

| | |
|---|---|
| Compound No. 26: | 10 |
| | 20 |
| Compound No. 27: | 10 |
| | 20 |
| Compound No. 24: | 20 |
| | 40 |
| Compound No. 33: | 10 |
| | 20 |
| Compound No. 35: | 20 |
| | 40 |
| Compound No. 36: | 10 |
| | 20 |
| Compound No. 38: | 10 |
| | 20 |
| Compound No. 44: | 20 |
| | 40 |
| Compound No. 55: | 10 |
| | 20 |

UNITED STATES PATENT OFFICE
CERTIFICATE OF CORRECTION

Patent No. 4,148,625  Dated April 10, 1979

Inventor(s) Hiroshi Nagase

It is certified that error appears in the above-identified patent and that said Letters Patent are hereby corrected as shown below:

Column 16, Table 2 corrected entries continued:

Compound No. 56:    10
                                    20

Compound No. 57:    10
                                    20

Compound No. 58:    10
                                    20

Compound No. 59:    10
                                    20

Column 18, Table 3: The compound numbers are not grouped with the correct "Dose g/are". The corrected entries are as follows:

Compound No. 1:    10
                                   20

Compound No. 14:    20
                                   40

Compound No. 27:    10
                                   20

UNITED STATES PATENT OFFICE
CERTIFICATE OF CORRECTION

Patent No. 4,148,625  Dated April 10, 1979

Inventor(s) Hiroshi Nagase

It is certified that error appears in the above-identified patent and that said Letters Patent are hereby corrected as shown below:

Column 18, Table 3 corrected entries continued:

|  |  |
|---|---|
| Compound No. 38: | 20 |
|  | 40 |
| Compound No. 56: | 10 |
|  | 20 |
| Compound No. 57: | 10 |
|  | 20 |
| Compound No. 58: | 10 |
|  | 20 |
| Compound No. 59: | 10 |
|  | 20 |
| Compound No. 55: | 10 |
|  | 20 |

Signed and Sealed this

Eighteenth Day of September 1979

[SEAL]

Attest:

LUTRELLE F. PARKER

Attesting Officer   Acting Commissioner of Patents and Trademarks are obtained from the corresponding compounds (III). (These compounds are shown in Table 1

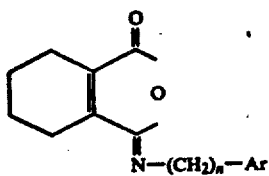

[wherein Ar and n are respectively as previously defined]

Table 1

| No | —(CH$_2$)$_n$—Ar | m.p. (°C) |
|---|---|---|
| 3 | C$_6$H$_5$—CH$_2$— | 93–94 |
| 4 | 2-Cl-C$_6$H$_4$—CH$_2$— | 114–115 |
| 5 | 4-Cl-C$_6$H$_4$—CH$_2$— | 117–118 |
| 6 | 2-CH$_3$-C$_6$H$_4$— | 97 |
| 7 | 3-CH$_3$-C$_6$H$_4$— | 68–69 |
| 8 | 4-CH$_3$-C$_6$H$_4$— | 103–104 |
| 9 | 4-n-C$_4$H$_9$-C$_6$H$_4$— | Oil B 0.05 170° C. |
| 10 | 4-C$_2$H$_5$-C$_6$H$_4$— | 59–60 |
| 11 | 4-(CH$_3$)$_3$C-C$_6$H$_4$— | 92.5–93.5 |
| 12 | 2-OCH$_3$-C$_6$H$_4$— | 122–124 |
| 13 | 3-CH$_3$O-C$_6$H$_4$— | 62 |
| 14 | 4-CH$_3$O-C$_6$H$_4$— | 99 |
| 15 | 3-C$_2$H$_5$O-C$_6$H$_4$— | 77–78 |
| 16 | 4-C$_2$H$_5$O-C$_6$H$_4$— | 88–89 |
| 17 | 4-(CH$_3$)$_2$CH-O-C$_6$H$_4$— | 88–89 |
| 18 | 4-n-C$_4$H$_9$O-C$_6$H$_4$— | 74 |
| 19 | 4-n-C$_5$H$_{11}$O-C$_6$H$_4$— | 59–61 |
| 20 | 4-n-C$_6$H$_{13}$O-C$_6$H$_4$— | 57–59 |
| 21 | 4-CH$_2$=CH—CH$_2$O-C$_6$H$_4$— | 61 |
| 22 | 3-CH$_2$=CH—CH$_2$O-C$_6$H$_4$— | 96–97 |
| 23 | 4-C$_6$H$_5$CH$_2$O-C$_6$H$_4$— | 121–123 |
| 24 | 4-(4-CH$_3$-C$_6$H$_4$-CH$_2$O)-C$_6$H$_4$— | 152–154 |
| 25 | 4-(4-O$_2$N-C$_6$H$_4$-CH$_2$O)-C$_6$H$_4$— | 155–156.5 |
| 26 | 4-(2,3-Cl$_2$-C$_6$H$_3$-CH$_2$O)-C$_6$H$_4$— | 132–133 |
| 27 | 4-(2,4-Cl$_2$-C$_6$H$_3$-CH$_2$O)-C$_6$H$_4$— | 118–119 |
| 28 | 3-HO-C$_6$H$_4$— | 138 |
| 29 | 4-HO-C$_6$H$_4$— | 147–148 |
| 30 | 4-O$_2$N-C$_6$H$_4$— | 105–106 |
| 31 | 2-CF$_3$-C$_6$H$_4$— | 98 |
| 32 | 4-CF$_3$-C$_6$H$_4$— | 64–65 |
| 33 | 4-NC-C$_6$H$_4$— | 95–97 |
| 34 | 4-CH$_3$S-C$_6$H$_4$— | 80–81 |
| 35 | 4-(4-Cl-C$_6$H$_4$-CH$_2$S)-C$_6$H$_4$— | 105–106 |
| 36 | 8-methyl-1-naphthyl | 134.5–135.5 |
| 37 | 3-OCH$_3$-4-CH$_3$-C$_6$H$_3$— | 88–90 |
| 38 | 3-Cl-4-CH$_3$-C$_6$H$_3$— | 96–97 |
| 39 | 4-Cl-3-CH$_3$-C$_6$H$_3$— | 88–89 |
| 40 | 2-Cl-3-CH$_3$-C$_6$H$_3$— | 113–115 |
| 41 | 3-Br-4-CH$_3$-C$_6$H$_3$— | 97–99 |
| 42 | 3-Cl-4-OCH$_3$-C$_6$H$_3$— | 97–98 |
| 43 | 3,4-(CH$_3$)$_2$-C$_6$H$_3$— | 121–122 |
| 44 | 3,5-(CH$_3$)$_2$-C$_6$H$_3$— | 94–95 |